(12) United States Patent
Benedetti et al.

(10) Patent No.: US 6,902,912 B2
(45) Date of Patent: Jun. 7, 2005

(54) PROCESS FOR PRODUCING GLUTATHIONE

(75) Inventors: Alberto Benedetti, Cernusco sul Naviglio (IT); Enrico Giuseppe Roberto Berardi, Orosei (IT); Matilde Manzoni, Segrate+Milan (IT); Marina Nichele, Vanzaghello (IT); Hermes Pagani, Sesto San Giovanni (IT); Manuela Rollini, Corsico (IT)

(73) Assignee: Gnosis Srl, Cairate (IT)

(*) Notice: Subject to any disclaimer, the term of this patent is extended or adjusted under 35 U.S.C. 154(b) by 0 days.

(21) Appl. No.: 10/609,561

(22) Filed: Jul. 1, 2003

(65) Prior Publication Data
US 2004/0048337 A1 Mar. 11, 2004

(30) Foreign Application Priority Data
Aug. 9, 2002 (EP) .......................... 02017906

(51) Int. Cl.[7] .......................... C12P 21/04; C12P 21/06
(52) U.S. Cl. .................... 435/71.1; 435/68.1; 435/69.1; 435/171; 435/255.2; 435/255.21; 435/255.4; 435/255.5; 435/256.8
(58) Field of Search .............................. 435/71.1, 68.1, 435/69.1, 255.2, 255.21, 255.5, 255.4, 256.8, 171

(56) References Cited

U.S. PATENT DOCUMENTS 4,582,801 A * 4/1986 Hamada et al. ............ 435/71.1

FOREIGN PATENT DOCUMENTS

| EP | 0 146 265 | 6/1985 |
| FR | 2 692 280 | 12/1993 |

OTHER PUBLICATIONS

C. Alfafara, et al., Applied Microbiology and Biotechnology, vol. 37, No. 2, XP–001032594, pp. 141–146, "Cysteine Addition Strategy for Maximum Glutathione Production in Fed–Batch Culture of *Saccharomyces cerevisiae*", 1992.

C. G. Alfafara, et al., Applied Microbiology and Biotechnology, vol. 36, No. 4, XP–008012042, pp. 538–540, "Effect of Amino Acids on Glutathione Production by *Saccharomyces cerevisiae*", 1992.

G. R. Willsky, et al., Journal of Cellular Biochemistry–Supplement, No. 21A, XP–002179477, p. 251, "Vanadate Metabolism in *Saccharomyces cerevisiae*", 1995.

H. Shimizu, et al., Biotechnology and Bioengineering, vol. 38, XP–002179478, pp. 196–205, "Optimal Production of Glutathione by Controlling the Specific Growth Rate of Yeast in Fed–Batch Culture", 1991.

Derwent Publications, AN 1986–078827, XP–002179483, JP 61–027999, Feb. 7, 1986.

Derwent Publications, AN 1974–42553V, XP–002179481, JP 49–014680, Feb. 8, 1974.

Derwent Publications, AN 1978–11596A, XP–002179480, JP 52–156994, Dec. 27, 1977.

* cited by examiner

Primary Examiner—Herbert J. Lilling
(74) Attorney, Agent, or Firm—Oblon, Spivak, McClelland, Maier & Neustadt, P.C.

(57) ABSTRACT

There is disclosed a fermentation process for producing glutathione which comprises (a) the obtainment of a biomass pre-culture by pre-cultivating, in aerobic conditions, a strain of a glutathione producing yeast wherein the glutathione content per biomass unit is higher than 1.2% w/w; (b) the cultivation, in aerobic conditions, of the resulting biomass pre-culture such that the resulting biomass density is higher than 50 g/l; (c) the activation of the cultured biomass; and (d) the recovery of the cultured biomass, extracting glutathione at a pH equal to or lower than 6 and purifying the resulting glutathione. The process allows to obtain glutathione with high yields and relatively low costs.

41 Claims, No Drawings

PROCESS FOR PRODUCING GLUTATHIONE

The present invention relates to a process for producing glutathione. Particularly, the invention concerns a fermentation and activation process for producing glutathione (hereinafter GSH) which allows to obtain GSH with high yields and relatively low costs.

GSH, also known as N-(N-L-γ-glutamyl-L-cysteinyl) glycine, is a known cellular tripeptide, present in virtually all cells. Its diverse functions are important to many biomedical fields, including enzymology, transport, pharmacology, therapy, toxicology, endocrinology and microbiology, as well as to agriculture.

GSH plays a crucial role in various metabolic districts, as well as in transport and in cellular protection. It serves the reduction of the disulfide linkages of proteins and other molecules, the synthesis of the deoxyribonucleotide precursors of DNA, and the protection of cells against the dangerous effects of free radicals and of the many reactive oxygen intermediates (e.g., peroxides) that are formed at various stages of metabolism. The enzymatic and transport phenomena of GSH metabolism are treated in: Meister "Selective Modification Of Glutathione Metabolism", Science, Volume 220, No. 4596, 472–477 (1983).

Increasing the intracellular GSH levels, in various human body districts, may be achieved by oral administration of pure GSH, or by injection of certain GSH monoesters after dissolution in water (see, for example, U.S. Pat. No. 4,710,489; U.S. Pat. No. 4,784,685 and U.S. Pat. No. 4,879,370).

GSH is produced industrially mainly by fermentation processes wherein the compound is extracted from microbial cells. Methods of producing GSH from microorganisms, are disclosed in various patents, including U.S. Pat. No. 4,596,775 and U.S. Pat. No. 4,582,801.

U.S. Pat. No. 4,582,801 discloses a process for producing GSH with high yields (about 3–4% on dry cells and about 0.7–0.9% g/l), involving cultivatiting a strain belonging to the genus *Saccharomyces*, and having both an ability to produce GSH and a resistance to 1,2,4-triazole or sodium azide, in a culture medium containing assimilable sources of carbon, nitrogen and inorganic salts, accumulating GSH in the microbial cells, harvesting the cells and recovering GSH therefrom.

FR-A-2,692,280 discloses the use of zinc-resistant yeasts, belonging to the genus *Saccharomyces*, in a fermentation process for producing GSH which is obtained in 4.1–6.6% on dry weight; the higher percentage is obtained using L-cysteine which is known to ameliorate the accumulation of GSH during the fermentation while negatively affecting the production of the biomass.

Udeh K. O. and Achremowicz B., in "High-glutathione containing yeast *Saccharomyces cerevisiae*: optimization of production", Acta Microbiologica Polonica, 1997, vol. 46, No. 1, 105–114 debate about how to maximize GSH yield using a high-GSH containing yeast *S. cerevisiae* S-8H and obtaining, a GSH average yield of 1.6 g/l and a GSH content of 17 mg/g dry biomass.

Chi-Hsien Liu et al. in "Medium optimization for glutathione production by *Saccharomyces cerevisiae*", Process Biochemistry, vol. 34, 1999, 17–23 report that glucose, peptone and magnesium sulphate are suitable components for the cell growth and GSH production in the yeast strain, the latter amounting, as an average, to 26–28 mg/l and to 124.93 mg/l as a maximum.

Alfafara C. et al. in "Cysteine addition strategy for maximum glutathione production in fed-batch culture of *Saccharomyces cerevisiae*", Appl. Microbiol. Biotechnol., 1992, 37, 141–146 teach to maintain a constant cysteine concentration in the reactor, during the fermentation, to maximize total GSH production amounting to about 0.8 g/l.

Although these processes already represent an improvement for the production of GSH, they are sometimes either too complex or their production yields are still relatively low, and a high production of biomass together with a specific productivity are still a goal for the production of GSH.

It has now been found that GSH can be produced by means of a fermentation process which comprises:

(a) the obtainment of a biomass pre-culture by pre-cultivating, in aerobic conditions, a strain of a yeast genus selected from *Saccharomyces, Hansenula, Pichia, Candida, Cryptococcus, Schizosaccharomyces, Sporobolomyces, Bullera, Bulleromyces, Fiilobasidiella, Lipomyces, Rhodotorula* or a stable mutant thereof, wherein the GSH content per biomass unit is higher than 1.2% w/w;

(b) the cultivation, in aerobic conditions, of the resulting biomass pre-culture such that the density of the resulting cultured biomass is higher than 50 g/l;

(c) the activation of the cultured biomass; and (d) the recovery of GSH from the cultured biomass resulting from step (c) by extracting GSH, at a pH equal to or lower than 6, and purifying the resulting GSH.

Particularly preferred as GSH producing yeasts are *Pichia angusta*, identified in our strain collection as GN/2219, filed on Jul. 13, 2000 with the "National Collection of Yeast Cultures" (NCYC), accession number: NCYC 2957; *Saccharomyces cerevisiae*, identified in our strain collection as GN/2220, filed on Jul. 13, 2000 with the NCYC, accession number: NCYC 2958; *Saccharomyces cerevisiae* var. ellipsoideus, identified in our strain collection as GN/2221, filed on Jul. 13, 2000 with the NCYC, accession number: NCYC 2959; *Candida boidinii*, mutant 21, identified in our strain collection as GN/2222, filed on Oct. 24, 2000 with the NCYC, accession number: NCYC 2983.

The yeast cells are either not mutagenized, or they can be treated with a mutagenic agent (e.g., UV light, 1-methyl-3-nitro-1-nitrosoguanidine (NTG), methanesulfonic acid ethyl ester (EMS), etc.). The yeast cells which may be used for the mutant selection may show an oxidative stress response lower than the one of the original wild strain, in a pathway which is different from the GSH response pathway.

*Pichia angusta*-NCYC 2957-GN/2219

The morphological, nutritional and sexual characteristics of this strain conform to those typical of this species, as described for instance in: Kurtzman & Fell, "The Yeasts, a taxonomy study" (4$^{th}$ edition) Elsevier, 1998.

In particular:

Morphological Characteristics

In 5% malt extract, after 3 days of incubation at 25° C., the cells are spheroidal, single, in pairs or in small clusters.

In Dalmau plate agar, after 7 days of incubation at 25° C. neither pseudohyphae nor hyphae are observed under the coverglass.

At 25° C., in 2% malt extract or YM medium (3 g/l yeast extract; 3 g/l malt extract; 5 g/l Bacto peptone—produced by Difco-; 10 g/l glucose; 20 g/l agar), ascospores are observed (ascospores are hat-shaped and usually non-conjugated).

|           | Fermentation |
|-----------|--------------|
| Glucose   | +            |
| Trehalose | +            |

-continued

| | |
|---|---|
| Galactose | − |
| Sucrose | − |
| Maltose | − |
| Lactose | − |
| Raffinose | − |

| Assimilation | | | |
|---|---|---|---|
| Sorbose (weak) | + | Mannitol | + |
| Sucrose | + | Glucitol | + |
| Maltose | + | α-methyl-D-glucoside | + |
| Trehalose | + | Salicin (weak) | + |
| Melezitose | + | Gluconate (weak) | + |
| Xylose | + | Succinate | + |
| Glycerol | + | Citrate | + |
| Erythritol | + | Nitrate | + |
| Ribitol | + | Vitamin-free medium | − |

Growth: 10% NaCl +; 5% Glucose +.

Other characteristics: starch is not observed; gelatin liquefaction is very weak; maximum growth temperature is 48° C.

*Saccharomyces cerevisiae*-NCYC 2958-GN/2220

The morphological, sexual and nutritional characteristics of this strain conform to those typical of these species, as described for instance in: J. A. Barnet et al.: YEAST: Characteristics and identification. Third ed. Cambridge University, 2000, in particular:

Growth in "Malt extract": after 3 days at 25° C. the cells are ellipsoidal to cylindrical. A sediment, occasionally a ring, is present.

After one month at 20° C., a sediment is present.

Growth on "Malt agar": after one month at 20° C., the streak culture is butyrous, cream to slightly brownish.

Formation of ascospores: the asci contain one to four ascospores.

Acetate agar is the best medium for inducing sporulation.

| Assimilation of carbon compounds | | | |
|---|---|---|---|
| Glucose | + | Dl-Lactate | − |
| Galactose | − | Glycerol | − |
| Ribose | − | Sorbitol | − |
| Saccharose | + | Erythritol | − |
| Maltose | + | Mannitol | − |
| Cellobiose | − | Inositol | − |
| Lactose | − | Sorbose | − |
| Melibiose | − | Glucuronate | − |
| Raffinose | + | Gluconate | − |
| Trehalose | − | Glucosamine | − |
| L-Arabinose | − | N-acetyl-glucosamine | − |
| D-xylose | − | α-methyl-D-glucoside | − |
| Ramnose | − | 2-Ketogluconate | − |
| Levulinate | − | Palatinose | + |
| Melezitose | − | Esculine | − |

| Fermentation | 3 days | 24 days |
|---|---|---|
| Cellobiose | − | − |
| Galactose | − | − |
| Glucose | + | + |
| Lactose | − | − |
| Maltose | + | + |
| Melibiose | − | − |
| Sucrose | + | + |
| Trehalose | − | − |

*Saccharomyces cerevisiae* var. *ellipsoideus*-NCYC 2959-GN/2221

The characteristics of this strain are identical to the ones reported above for *Saccharomyces cerevisiae*-NCYC 2958-, GN/2220, excepted both the assimilation of carbon compounds and the fermentation tests.

| Assimilation of carbon compounds | | | |
|---|---|---|---|
| Glucose | + | Dl-Lactate | − |
| Galactose | + | Glycerol | − |
| Ribose | − | Sorbitol | − |
| Saccharose | + | Erythritol | − |
| Maltose | + | Mannitol | − |
| Cellobiose | − | Inositol | − |
| Lactose | − | Sorbose | − |
| Melibiose | − | Glucuronate | − |
| Raffinose | + | Gluconate | − |
| Trehalose | − | Glucosamine | − |
| L-Arabinose | − | N-acetyl-glucosamine | − |
| D-xylose | − | α-methyl-D-glucoside | − |
| Ramnose | − | 2-Ketogluconate | − |
| Levulinate | − | Palatinose | + |
| Melezitose | − | Esculine | − |

| Fermentation | 3 days | 24 days |
|---|---|---|
| Cellobiose | − | − |
| Galactose | − | + |
| Glucose | + | + |
| Lactose | − | − |
| Maltose | + | + |
| Melibiose | − | − |
| Sucrose | + | + |
| Trehalose | − | − |

*Candida boidinii* (mutant 21)-NCYC 2983-GN/2222

The morphological, sexual and nutritional characteristics of this strain conform to those typical of these species, as described for instance in: J. A. Barnet et al.: YEAST: Characteristics and identification. Third ed. Cambridge University, 2000, in particular:

Growth in glucose-yeast extract-peptone water: after 3 days at 25° C. the cells are long-ovoid to cylindrical, after slightly curved.

Growth on glucose-yeast extract-peptone agar: after one month at 25° C. the streak culture is yellowish cream-coloured, soft, delicately wrinkled.

Dalmau plate culture on corn meal agar: the pseudo-mycelium is present and with short ramified hyphae which bear verticillated chains and groups of ovoidal blastospores.

| Assimilation of carbon compounds | | | |
|---|---|---|---|
| Glucose | + | Dl-Lactate | + |
| Galactose | − | Glycerol | + |
| Ribose | + | Sorbitol | + |
| Saccharose | − | Erythritol | + |
| Maltose | − | Mannitol | + |
| Cellobiose | − | Inositol | − |
| Lactose | − | Sorbose | − |
| Melibiose | − | Glucuronate | − |
| Raffinose | − | Gluconate | − |
| Trehalose | − | Glucosamine | − |
| L-Arabinose | − | N-acetyl glucosamine | +− |
| D-xylose | + | α-methyl-D-glucoside | − |
| Ramnose | − | 2-Ketogluconate | − |
| Levulinate | − | Palatinose | −+ |
| Melezitose | − | Esculine | − |

| Fermentation | 3 days | 24 days |
|---|---|---|
| Cellobiose | − | − |
| Galactose | − | − |
| Glucose | + | + |
| Lactose | − | − |
| Maltose | − | − |
| Melibiose | − | − |
| Sucrose | − | − |
| Trehalose | − | − |

The process of the invention provides an economic way for producing GSH, allowing to improve the productivity of the GSH producing yeasts as well as the rapid isolation of GSH overproducing mutants, the inexpensive cultivation of such mutants, the increase the GSH content of the biomass and the rapid and effective extraction of GSH from said biomass.

The cells of the yeast suitable for carrying out the process of the invention are haploid.

Either steps (a) and/or (b) and/or (c) of the process of the invention can be carried out in a nutrient aqueous, liquid or solid, medium comprising at least one of the following compounds:

(i) a compound of a metal selected from Cd, V, Cu, Fe, Pb, Al, Co, Cr, Mn, Ni, Mo, Hg;

(ii) a peroxyde (e.g., $H_2O_2$, t-butyl peroxide, etc.);

(iii) an aldehyde (e.g., methylglyoxal, formaldehyde, acetaldehyde, etc.);

(iv) a hydroperoxyde (e.g., t-butyl-HOOH, etc.);

(v) a fatty acid (e.g., oleic acid, linolenic acid, arachidonic acid, etc.) and/or a linear or branched, saturated or unsaturated, derivative thereof;

said medium further comprising at least an assimilable source of carbon and/or nitrogen and/or at least a mineral salt, whenever the compounds (i) to (v) are not such a source and/or salt themselves.

The sources of carbon can come, for instance, from agricultural and/or industrial wastes; particularly, they can comprise at least one of the following substances: sugars, such as dextrose, dextrin, glucose, fructose, saccharose, mannitol, mannose; organic acids; alcohols; aldehydes; glycerol; starch; fats; oils; hydrocarbons and whey and the like; particularly, the production of GSH in accordance with the invention can be carried out under favourable conditions employing relatively non-expensive carbon sources, such as beet molasses.

The nitrogen sources can comprise, for instance, at least one of the following substances: malt extract, corn steep liquor, enzymatic hydrolysate of casein, soya flour, dry yeast, peptone, soy peptone, meat extract, nitrate, amino acids, casein, ammonium salts and the like. Good results are obtained using ammonium salts such as ammonium nitrate and ammonium sulphate.

The mineral salts used for the production can vary depending on the culture medium; the soluble inorganic salts which provide sodium, potassium, magnesium, sulphate, chloride, nitrate ions, can be used. Such salts can be, for instance, monobasic potassium phosphate, magnesium sulphate, monobasic potassium sulphate, sodium nitrate. The addition of calcium carbonate may also be useful.

Further, the medium may comprise at least an amino acid (e.g. cysteine, methionine, glutamate, glutamine, glycine, leucine, acetylcysteine etc.) and/or a phosphorus source (e.g., potassium phosphate, etc.) and/or an alcohol (methanol, ethanol, isopropanol, butanol, etc.)

Preferably, in step (a), the GSH content per biomass unit is higher than 1.6% w/w whereas step (b) is preferably carried out at 20–50° C. for 12–72 h, particularly at 25–45° C. for 12–48 h; the density of the cultured biomass being preferably between 50 and 65 g/l.

The process of the invention and, specifically, either steps (a) and/or (b) and/or (c), may be carried out either batch-wise or continuously.

Steps (a) and/or (b) and/or (c) of the process of the invention can be carried out by aeration with either air or oxygen gas and/or a mixture thereof; the process of the invention is advantageously carried out in aerated fermenters in order to get remarkable amounts of GSH. The preferred fermenter is an aeration agitation-type or an air-lift fermenter. Further, the process can be carried out in a flask and in fermenters of different capacity.

The process of the invention encompasses the activation—step (c)—of the cultured biomass. In the present specification, "activation" is meant to indicate an enrichment of the intracellular GSH content of the biomass carried out employing resting cells in non-growing conditions.

Advantageously, the activation comprises:

($\alpha$) resuspending the cultured biomass, for instance, 5–20% of the dry biomass, in a water solution containing a 0.4–1 M carbon source;

($\beta$) stirring the resulting suspension at 300–600 rpm; and ($\gamma$) aerating said suspension with either air or oxygen gas and/or a mixture thereof, preferably at 1–4 vvm.

Preferably, in step (a), the water solution contains 0.001–0.01 M cysteine, glycine and glutamate.

In another preferred embodiment, GSH, in step (d) of the process of the invention, is extracted by lysis at a pH of 0.5–3.0 and at a temperature of 70–90° C.

The cultivated biomass resulting from step (b) shows a productivity of GSH from about 0.9–1.2% whereas the activated cultured biomass resulting from step (c) of the process of the invention shows an increase of the GSH productivity to 2.7–3.9% under dried conditions.

The extraction of GSH in step (d) can be advantageously carried out through a strong cationic resin such as, for instance, Amberlite® IR 120-200-220 produced by Rhom & Haas or Relite® CF produced by Mitsubishi Chemical Corporation and, subsequently, a non-ionic resin such as, for instance, SP 207 (Resindion, Mitsubishi). The GSH extraction can be preferably obtained through precipitation of the salt, in the presence of $H_2SO_4$ in which the salt, after salification of a $H_2SO_4$ becomes insoluble.

The following examples illustrate the invention without limiting it.

EXAMPLE 1

One wild strain of *Pichia angusta* isolated from soil samples was used, namely a homothallic haploid.

Stage 1

The strain was cultured for 20 hours at 37° C. (250 ml conical flasks, 200 rpm orbital incubation) in 100 ml Rich Medium (RM) having the following composition (g/l):

| | |
|---|---|
| Glucose | 20 |
| Peptone | 20 |
| Yeast Extract | 10 |

Stage 2

25 ml of yeast culture were spin-washed in distilled water twice and re-suspended in distilled water.

$5 \times 10^7$ cells were plated out onto Glucose Mineral Medium (GM) containing 8 mM cadmium chloride monohydrate (MMC) and having the following composition (g/l):

| | |
|---|---|
| Glucose | 20 |
| Yeast Nitrogen Base | 7 |
| Cadmium chloride monohydrate | 1.61 |

The plates were UV irradiated to 90% mortality and incubated at 37° C. in the dark, for 20 days.

Stage 3

After incubation, a typical plate showed 800–1000 colonies, about 50% of which had a diameter F<1 mm ("small") and about 50% had F>1 mm ("large"). Ten large colonies were isolated, streak purified onto RM plates, and re-tested onto MMC. Five out of ten colonies confirmed their cadmium-resistant phenotype.

Stage 4

Five colonies isolated in stage 3 were treated as described above yet, in this case, the cadmium was replaced with 200 mM of sodium orthovanadate. At the end, five colonies were isolated confirming their cadmium-vanadate-resistant phenotype.

Stage 5

Each of the five cadmium-vanadate-resistant colonies of the previous stage (hereinafter CVCdA, CVCdB, CVC, CVD, CVE) were pre-cultured in 7.5 ml Mineral Medium (MM) and incubated 16 h at 37° C. (orbital, 200 rpm). Cells from these pre-cultures were then used to inoculate 100 ml flasks containing 20 ml MM, so as to start with $5 \times 10^6$ cells/ml. The flasks were incubated at 37° C. for 24 h (orbital, 200 rpm); the experiment was done in triplicate.

Stage 6

The cell content of each flask was collected by centrifugation, washed twice, and divided into two aliquots. One aliquot served to determine the dry weight of the biomass, whereas the other served to determine the GSH content of cell extracts, obtained by re-suspending the cell in 1 ml perchloric acid, adding 0.5 g glass beads (Sigma #G-9268), stirring 1 min×3, precipitating the solid phase by centrifugation, and pipetting on the extract, according to the method of Akerboom and Sies "Methods in enzymology", vol. 27, pp.373–384, 1981, Academic Press Inc.

Table 1 shows some significant results obtained with the five cultures, expressed as percentage of the weight levels per unit biomass.

TABLE 1

| | GSH/biomass unit | | | |
|---|---|---|---|---|
| Strain | E. 1 | E. 2 | E. 3 | Mean |
| Wild type (control) | 100 | 100 | 100 | 100 |
| Mutant CVCdA | 124 | 119 | 122 | 122 |
| Mutant CVCdB | 231 | 219 | 242 | 231 |
| Mutant CVC | 100 | 101 | 97 | 99 |
| Mutant CVD | 102 | 105 | 106 | 104 |
| Mutant CVE | 109 | 110 | 107 | 109 |

E. = Experiment

It will be noted that mutants CVCdA and, remarkably, CVCdB (*Pichia angusta*, identified in our strain collection as GN/2219, NCYC 2957) show a significant increase in the intracellular GSH content.

Stage 7

The production of GSH using mutant CVCdB GN/2219, NCYC 2957 indicated in Table 2 as mutant B, in a 3 l fermenter was carried out employing two different media (GM, GlyM—as GM, yet glucose is replaced by 2% glycerol—and mM—as GM, yet glucose is replaced by 18% molasses, corresponding to 9% as saccharose), and the following culture conditions: volume: 2 l, temperature: 35° C., air: 1 vvm, pH: 5.0.

The evolution of GSH and biomass was followed for 62 h, and compared to that of an identical control culture (wild strain). The results are shown in Table 2.

TABLE 2

| | Biomass evolution (dry weight) g | | | | | | GSH evolution MG/g (dry weight) | | | | | |
|---|---|---|---|---|---|---|---|---|---|---|---|---|
| | Wild type (control) | | | Mutant B | | | Wild type (control) | | | Mutant B | | |
| Medium | GM | Gly M | mM | GM | Gly M | mM | GM | Gly M | mM | GM | Gly M | mM |
| Start | 0.002 | 0.002 | 0.002 | 0.002 | 0.002 | 0.002 | — | — | — | — | — | — |
| 14 h | 0.4 | 0.4 | 12.3 | 0.4 | 0.4 | 12.1 | 0.9 | 0.8 | 0.8 | 2.1 | 2.3 | 2.4 |
| 24 h | 4.1 | 4.5 | 37.4 | 4.2 | 4.3 | 37.7 | 9.8 | 9.7 | 9.7 | 17.8 | 16.8 | 17.1 |
| 38 h | 5.3 | 5.7 | 54.2 | 5.4 | 5.5 | 53.3 | 7.8 | 7.9 | 7.8 | 16.1 | 17.1 | 17.2 |
| 41 h | 6.4 | 6.6 | 55.1 | 6.7 | 6.7 | 55.4 | 4.5 | 4.3 | 4.6 | 8.4 | 7.9 | 15.9 |
| 62 h | 12.7 | 12.6 | 59.7 | 12.9 | 12.7 | 59.5 | 2.7 | 3.1 | 3.2 | 5.1 | 5.4 | 13.3 |

It will be noted that the cellular productivity is higher in the case of the Mutant B than in the wild strain, whereas the yield differences between the two media are not relevant.

These tests show that the process of the invention can be carried out under favourable conditions employing various media and for long periods of time.

After the fermentation phase, the biomass was recovered, washed and then either re-suspended in a concentrated form to start an activation stage, aiming at furtherly increase GSH yields (described in example 2), or processed to extract and purify GSH (herebelow described in stage 8).

Stage 8

The biomass obtained from the previous stage was re-suspended in demineralised water to a concentration of 7 g/l (biomass dry weight). 10 liters of this concentrated biomass suspension (CoBS) were permeabilised using a combination of low pH (1–6.5, with concentrated $H_2SO_4$) and high temperature (75° C.×3 min). The biomass was then removed by filtration (0.2 mm ceramic membranes), and the GSH containing solution was concentrated by reverse osmosis so as to reach about 6 g/l GSH.

Tab. 3 summarizes the GSH yields (%) obtained at various pH, using the aforementioned CoBS.

TABLE 3

| pH   | 6.5  | 5    | 4    | 3    | 1.5  |
|------|------|------|------|------|------|
| E. 1 | 0.50 | 0.55 | 0.61 | 0.68 | 0.98 |
| E. 2 | 0.48 | 0.52 | 0.58 | 0.72 | 1.02 |
| E. 3 | 0.42 | 0.49 | 0.64 | 0.73 | 0.95 |

E. = Experiment

These tests show that, under the conditions employed, cell permeabilisation is favoured by low pHs.

Stage 9

The purification of GSH was achieved by percolating 1 l of the concentrated GSH solution (about 6 g/l) in a column packed with Amberlite (1 l, IR120H), at a flow rate of 1 BV/h. 30 BV of demineralised water are then applied to wash the resin, before eluting the GSH with 1% $H_2SO_4$. 6 l of the resulting eluates are concentrated to 5 l by reverse osmosis, yielding about 85% of the initial GSH.

Stage 10

The concentrated eluates were percolated in a column packed with 1 l of non-ionic porous resin i.e. SP207 (Resindion, Mitsubishi), previously regenerated at 1 BV/h. GSH was then eluted with water, and fractions 2 to 9 were collected. The GSH aqueous solution thus obtained was concentrated to 500 g/l. GSH was finally precipitated by a 50% ethanol solution. 4 g of white crystalline powder was obtained, with 98% GSH content.

EXAMPLE 2

A non sporulating spontaneous mutant strain of *Saccharomyces cerevisiae* (identified in our strain collection as GN/2220, NCYC 2958), having a GSH content per biomass unit higher than 1.4% w/w, was used.

Stage 1

The strain was batch cultured for 24 h in a 14 l fermenter employing three different media, namely (amounts are expressed as g/l) YP (20 peptone, 10 yeast extract, 10 glycerol, pH 5), YPG (20 peptone, 10 yeast extract, 20 glucose, pH 5) and B (60 beet molasses—equivalent to 30 sucrose-, 5 $(NH_4)_2SO_4$, 1 $K_2HPO_4$, 0.5 yeast extract, 0.2 $MgSO_4$, pH 5.8). Cultivation conditions were as follows: 28° C., 1 vvm air, 400 rpm. Antifoam: Sigma PPG #2000 Inoculum 10% (V/V) of a stationary-phase flask culture in YP.

Table 4 summarizes the results of seven different batches.

TABLE 4

|    |     | Biomass |      | GSH  |      |      |
|----|-----|---------|------|------|------|------|
|    |     | Y1      | P    | Y1   | Y2   | P    |
| E. | M   | g/l     | g/lh | mg/l | %    | mg/lh |
| 1  | YPG | 9.40    | 0.39 | 94   | 1.0  | 3.90 |
| 2  | YPG | 9.20    | 0.39 | 65   | 0.7  | 2.70 |
| 3  | B   | 10.7    | 0.44 | 207  | 1.9  | 8.60 |
| 4  | B   | 9.10    | 0.38 | 155  | 1.7  | 6.50 |
| 5  | B   | 10.5    | 0.44 | 203  | 1.9  | 8.46 |
| 6  | YP  | 7.50    | 0.31 | 90   | 1.2  | 3.80 |
| 7  | YP  | 7.80    | 0.32 | 101  | 1.2  | 4.00 |

E. = Experiment; P = Productivity; Y1 = yield per volume; Y2 = yield per dry biomass; no residual sucrose was detected.

It will be noted that the cellular productivity, in the case of the medium B is more than double than in the case of the other two media; also the relative final yields, which differ considerably among the three media, show that B allows to obtain the best results.

Stage 2

Biomass obtained from the previous stage was collected by centrifugation at 10,000 rpm for 10 min (5° C.), washed twice with deionized water and re-suspended to 7% concentration (dry biomass, w/v) in the following solution (g/l):

| Glucose          | 82  |
| Sodium tartrate  | 10  |
| Adenine          | 4   |
| Cysteine         | 4   |
| Methionine       | 3.5 |
| $KH_2PO_4$       | 3.5 |

The "biomass activation" process was then started in a 3 l fermenter for 24 h, with the following operating conditions: agitation speed, 500 rpm; aeration rate, 3 vvm; temperature, 28° C.

Table 5 summarizes the GSH yields of four activation experiments, employing biomass obtained either in B medium, or in YPG medium.

TABLE 5

|    |                     | GSH Yield (% of dry biomass) ||
|    | Fermentation        | Before     | After      |
| E. | medium              | activation | activation |
| 1  | YPG                 | 1.0        | 2.0        |
| 2  | YPG                 | 0.7        | 2.0        |
| 3  | B                   | 1.9        | 3.7        |
| 4  | B                   | 1.7        | 3.4        |

E. = Experiment

It will be noted that, independently of the initial GSH content, the aforementioned 24 h activation process allows significant GSH yield increases.

EXAMPLE 3

The strain of *Saccharomyces cerevisiae* NCYC 2958 was batch cultured for 30 h in a 50 l fermenter using the medium B (example 2). Inoculum 20% of stationary-phase. Cultivation conditions were as in the example 2.

During the growth, starting form the 12th h, five additions (every 3 h) of molasses were done, so that the concentration of saccharose was kept higher than 10% until the 24th h.

A biomass of 58.89 g/l and 1.45% of GSH both on dry weight were obtained.

The biomass collected for centrifugation (example 2), was suspended again at 10% and "activated" in the following solution (g/l):

| Glucose           | 82      |
| Sodium tartrate   | 10      |
| Adenine           | 4       |
| Cysteine          | 4       |
| Sodium glutamate  | 5       |
| Glycine           | 5       |
| Methionine        | 3       |
| 85% $H_3PO_4$     | 0.25 ml |

At the same conditions of example 2, 3.7% GSH was obtained under dry conditions, equal to 3.7 g/l of "activation".

EXAMPLE 4

One wild strain of *Candida boidinii*, isolated from plant material, was mutagenised, and mutant #21 was selected following a procedure analogous to the one described in Example 1, but using methylglioxal as a selective agent. This strain was identified as *Candida boidinii* mutant 21, NCYC 2983, internal strain collection GN/2222, and showed a GSH content per biomass unit higher than 1.5% w/w.

Stage 1

The strain was batch cultured for 24 h in a 14 l fermenter employing medium B, but the molasses were added until 180 g/l (90 g/l as saccharose) as in example 3). Cultivation conditions were as follows: 28° C., 1 vvm air, 400 rpm. Antifoam: Sigma PPG # Inoculum 10% (v/v) of a stationary-phase flask culture in YP.

Table 6 summarizes the results of the fermentation.

TABLE 6

| H | Biomass | | GSH | | |
|---|---|---|---|---|---|
| | Y1 g/l | P g/lh | Y1 mg/l | Y2 % | P mg/lh |
| 6 | 0.54 | 0.09 | 2.7 | 0.5 | 0.33 |
| 18 | 16.2 | 0.9 | 194.4 | 1.2 | 10.80 |
| 24 | 29.2 | 1.2 | 408.8 | 1.4 | 17.03 |
| 30 | 36.1 | 1.2 | 469.3 | 1.3 | 15.64 |

H = Hours; P = Productivity; Y1 = yield per volume; Y2 = yield per dry biomass; no residual sucrose was detected.

Stage 2

The biomass obtained from the aforementioned batch was treated as described in Example 1 (stage 8) in order to obtain a concentrated GSH solution (about 6 g/l). 1 l of this solution was adjusted to pH 1.8 by $H_2SO_4$, and then treated with a 10 ml suspension containing 1.4 g of $Cu_2O$ in water. The suspension was dropped very gently while the temperature was maintained at 4° C. The solution was then gently stirred at 4° C. for 2 h, and then undisturbed overnight.

Stage 3

After filtering, the precipitate (9 g) was washed several times with diluted $H_2SO_4$ and then solubilised by $H_2S$ at room temperature. The solution, containing 4.5 g of GSH was applied to 1 l of SP 207, a non ionic resin produced by Mitsubishi Chemical, and then eluted with 10 BV of demineralised water. Fractions were collected (6 l), concentrated and treated with 50% ethanol in water to precipitate GSH. 3.5 g of GSH, showing a 99% purity, were obtained.

EXAMPLE 5

The biomass obtained according to the examples 1 and 4 was treated as described in the example 1 (stage 8) in order to obtain a concentrated solution of GSH (about 6 g/l). 1 l of this solution was adjusted at pH 1.8 by $H_2SO_4$ and heated at 40° C. in waterbath.

At a temperature of 40° C., 10 ml of a $Cu_2O$ suspension (1.5 g) were added into water.

After 3 minutes, the resulting solution was quickly brought at 4° C. and then kept under agitation for 2 hours.

After 2 hours, it was proceeded to filtration as in the example 3 (stage 3). After filtration, the precipitate (0.5 g) was dissolved in $H_2S$, purified with SP 207, a non ionic resin produced by Mitsubishi Chemical, and precipitated in ethanol. 3.6 g of GSH, having a 99% purity, were obtained.

What is claimed is:

1. A fermentation process for producing glutathione which comprises:
   (a) obtaining a biomass pre-culture by pre-cultivating, in aerobic conditions, a strain of at least one yeast genus selected from *Saccharomyces, Hansenula, Pichia, Candida, Cryptococcus, Schizosaccharomyces, Sporobolomyces, Bullera, Bulleromyces, Filobasidiella, Lipomyces, Rhodotorula* or a stable mutant thereof, wherein the glutathione content per biomass unit is higher than 1.2% w/w;
   (b) cultivating, in aerobic conditions, of the resulting biomass pre-culture such that the density of the resulting cultured biomass is higher than 50 g/l;
   (c) activating the cultured biomass by resting the cells in non-growing conditions; and
   (d) recovering glutathione from the cultured biomass resulting from step (c) by extracting glutathione, at a pH equal to or lower than 6, and optionally purifying the resulting glutathione.

2. The process of claim 1, wherein the strain is *Pichia angusta*-NCYC 2957-(GN/2219).

3. The process of claim 1, wherein the strain is *Saccharomyces cerevisiae*-NCYC 2958-(GN/2220).

4. The process of claim 1, wherein the strain is *Saccharomyces cerevisiae* var. ellipsoideus-NCYC 2959-(GN/2221).

5. The process of claim 1, wherein the strain is *Candida boidinii*, mutant 21-NCYC 2983-(GN/2222).

6. The process of claim 1, wherein either steps (a) and/or (b) and/or (c) are carried out in an aqueous, liquid or solid nutrient medium comprising at least one of the following compounds:
   (i) a compound of a metal selected from Cd, V, Cu, Fe, Pb, Al, Co, Cr, Mn, Ni, Mo, or Hg;
   (ii) a peroxide;
   (iii) an aldehyde;
   (iv) a hydroperoxide;
   (v) a fatty acid and/or a linear or branched, saturated or unsaturated, derivative thereof;
   said medium further comprising at least one assimilable source of carbon and/or nitrogen and/or at least a mineral salt, whenever the compounds (i) to (v) are not such a source and/or salt themselves.

7. The process of claim 6, wherein the compound (i) is a mineral inorganic water soluble salt.

8. The process of claim 6, wherein the medium comprises at least an amino acid and/or a phosphorus source and/or an alcohol.

9. The process of claim 1, wherein, in step (a), the glutathione content per biomass is unit higher than 1.6% w/w.

10. The process of claim 1, wherein step (b) is carried out at 20–50° C. for 12–72 h and the density of the resulting cultured biomass is between 50 and 65 g/l.

11. The process of claim 1, wherein step (b) is carried out at 25–45° C. for 12–48 h.

12. The process of claim 1, wherein either steps (a) and/or (b) and/or (c) are carried out batch-wise or continuously.

13. The process of claim 6, wherein the carbon source comes from agricultural and/or industrial wastes.

14. The process of claim 13, wherein the carbon source comprises at least one of the following substances: sugar(s), organic acid(s), alcohol(s), aldehyde(s), glycerol, fat(s), oil(s), hydrocarbon(s) or whey.

15. The process of claim 13, wherein the carbon source comprises beet molasses.

16. The process of claim 6, wherein the nitrogen source comprises at least one of the following substances: malt extract, corn steep liquor, enzymatic hydrolysate of casein, soya flour, dry yeast, peptone, soy peptone, meat extract, nitrate, amino acids, casein or ammonium salt(s).

17. The process of claim 16, wherein the nitrogen source comprises ammonium nitrate or ammonium sulphate.

18. The process of claim 1, wherein either steps (a) and/or (b) and/or (c) are carried out by aeration with air or oxygen gas and/or a mixture thereof.

19. The process of claim 1, wherein activating comprises:
   ($\alpha$) resuspending the cultured biomass (5–20% dry biomass) a water solution containing a 0.4–1 M carbon source;
   ($\beta$) stirring the resulting suspension at 300–600 rpm; and
   ($\gamma$) aerating said suspension with air or oxygen gas and/or a mixture thereof.

20. The process of claim 19, wherein, in step ($\alpha$), the water solution contains 0.001–0.01 M cysteine, glycine and glutamate.

21. The process of claim 1, wherein the fermenter to be used is an aeration-agitation or an airlift fermenter.

22. The process of claim 21, wherein the glutathione in step (d) is extracted by lysis at a pH of 0.5–3.0 and at a temperature of 70–90° C.

23. The process of claim 1, wherein the glutathione in step (d) is extracted through a strong cationic resin and, subsequently, a non-ionic resin.

24. The process of claim 1, wherein said cultivated organism is *Saccharomyces*.

25. The process of claim 1, wherein said cultivated organism is *Hansenula*.

26. The process of claim 1, wherein said cultivated organism is *Pichia*.

27. The process of claim 1, wherein said cultivated organism is *Candida*.

28. The process of claim 1, wherein said cultivated organism is *Cryptococcus*.

29. The process of claim 1, wherein said cultivated organism is *Schizosaccharomyces*.

30. The process of claim 1, wherein said cultivated organism is *Sporobolomyces*.

31. The process of claim 1, wherein said cultivated organism is *Bullera*.

32. The process of claim 1, wherein said cultivated organism is *Bulleromyces*.

33. The process of claim 1, wherein said cultivated organism is *Filobasidiella*.

34. The process of claim 1, wherein said cultivated organism is *Lipomyces*.

35. The process of claim 1, wherein said cultivated organism is *Rhodotorula*.

36. The process of claim 1, further comprising purifying the glutathione.

37. The process of claim 1, wherein (a), (b) and/or (c) is carried out in a nutrient medium comprising at least one of Cd, V, Cu, Fe, Pb, Al, Co, Cr, Mn, Ni, Mo or Hg.

38. The process of claim 1, wherein (a), (b) and/or (c) is carried out in a nutrient medium comprising at least one peroxide.

39. The process of claim 1, wherein (a), (b) and/or (c) is carried out in a nutrient medium comprising at least one aldehyde.

40. The process of claim 1, wherein (a), (b) and/or (c) is carried out in a nutrient medium comprising at least one hydroperoxide.

41. The process of claim 1, wherein (a), (b) and/or (c) is carried out in a nutrient medium comprising at least one fatty acid.

* * * * *